(12) United States Patent  
Goliszek et al.

(10) Patent No.: US 7,502,234 B2  
(45) Date of Patent: Mar. 10, 2009

(54) PLANAR TRANSFORMER POWER SUPPLY

(75) Inventors: Gregory Goliszek, Oldsmar, FL (US); Nickolay Dimitrov Shilev, Sofia (BG)

(73) Assignee: Aaron Medical Industries, Inc., St. Petersburg, FL (US)

( * ) Notice: Subject to any disclaimer, the term of this patent is extended or adjusted under 35 U.S.C. 154(b) by 112 days.

(21) Appl. No.: 11/485,147

(22) Filed: Jul. 12, 2006

(65) Prior Publication Data

US 2008/0013350 A1 Jan. 17, 2008

(51) Int. Cl.
*H02M 3/335* (2006.01)

(52) U.S. Cl. .............................. 363/17; 336/200; 600/34

(58) Field of Classification Search ............ 363/16–20, 363/21.04, 21.06, 24–25, 97, 98, 132; 336/200, 336/206, 223, 229, 232; 600/34, 37–41
See application file for complete search history.

(56) References Cited

U.S. PATENT DOCUMENTS 6,807,069 B2 * 10/2004 Nieminen et al. ............. 363/17
6,987,678 B2 * 1/2006 Giandalia et al. ............. 363/86

* cited by examiner

*Primary Examiner*—Rajnikant B Patel
(74) *Attorney, Agent, or Firm*—Arthur W. Fisher, III

(57) ABSTRACT

A planar transformer power supply for an electrosurgical device to minimize stray capacitance comprising a step down/step-up isolation transformer and circuitry to limit the effects of a short circuit in the output of the planar transformer power supply on the input to the planar transformer power supply to enhance power capacity at a low load impedance as low as from about 5 ohms to about 10 ohms and to operate at resonance at the output of the planar transformer power supply.

1 Claim, 3 Drawing Sheets

PLANAR TRANSFORMER POWER SUPPLY

BACKGROUND OF THE INVENTION

1. Field of the Invention

A planar transformer for an electrosurgical device to minimize stray capacitance.

2. Description of the Prior Art

A common problem in the field of electro-surgery is the leakage of HF current. This leakage depends in large part on stray capacitance. A significant portion of this stray capacitance is attributable to the output transformer of the electro-surgical device or RF unit. Thus, stray capacitance can be reduced or minimized through the proper design of the transformer.

U.S. Pat. No. 4,255,735 discloses a device for transforming an alternating current-voltage which including a core, a primary winding subassembly and a second winding subassembly. One or both of the primary and second winding subassemblies consists of at least one pair of equal turn and approximately equal resistance windings wrapped co-directionally around the core, each having an equal number of tapped sections. A special tandem switch selectively interconnects tapped sections within winding pairs to provide a desired output terminal winding array such that all sections connected through the switch are energized, and are in the current carrying path at all selected switch positions. The primary and secondary windings are asymmetrically disposed in relation to each other while the leakage reactance is unequal when connected to place less than all of the tapped sections of each in parallel.

U.S. Pat. No. 4,547,721 shows a transformer structure having three cores disposed to define two transformer winding carriers. Each core comprises a pair of C-shaped sections to form pairs of legs joined by connecting portions. A first leg of the first core and a second leg of the second core delimit one of the transformer winding carriers. A third leg of the second core and a fourth leg of the third core delimit the other transformer winding carriers. The winding includes a primary transformer winding having at least a first coil and a second coil, and a secondary transformer winding having a first and a second coil. The first coils of the primary and second winding are wound along the first transformer winding carrier while the second coils of the primary and secondary transformer windings are wound along the second transformer winding carrier. The primary coils are wound in parallel in such a way that the AC voltage polarity in the two primary coils is 180 degrees out of phase with respect to one another and the AC voltage polarity in the two secondary coils is 180 degrees out of phase with respect to one another.

U.S. Pat. No. 6,154,376 describes reveals a high-frequency, high-density power conversion system providing loss less power switching with a single or double-ended power converter.

U.S. Pat. No. 6,529,389 shows a transformer comprising a primary coil, a secondary coil and a magnetic core. The secondary coil configured to provide a regulated DC output voltage and/or current. The primary coil operates the transformer as a low voltage input converter and as a high voltage input converter.

2002/01545520 teaches a universal switching power supply for generating one or more output voltage levels operable over a range of AC and DC input supply voltages. The universal switching power supply includes an intrinsically safe output, comprising a multi-layer PCB with a planar core transformer.

Additional examples of the prior art are found in U.S. Pat. Nos. 3,299,384 and 4,999,597.

SUMMARY OF THE INVENTION

The present invention relates to a split transformer to minimize the stray capacitance and reduce the negative effects of the other operating parameters commonly associated by transformers. In particular, the present invention relates to a planar push-pull output transformer and circuit.

The input section comprises a primary winding; while, the output section comprises a secondary winding. A transformer core section is disposed in operative relationship relative to the primary and secondary windings.

The transformer core section comprises a first core and a second core disposed in operative relationship relative to the primary winding and the secondary winding respectively and inductively coupled to each other by windings to cooperatively form a step-down transformer segment and a step-up transformer segment.

There are a number of operating advantages inherent in the step-down/step-up transformer configuration including minimizing the stray capacitance to about 5 pF.

In addition, the use of planar ferrite cores allows cooling heat-sinks to be attached easily to the flat surface of the planar core.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

Figure 1:
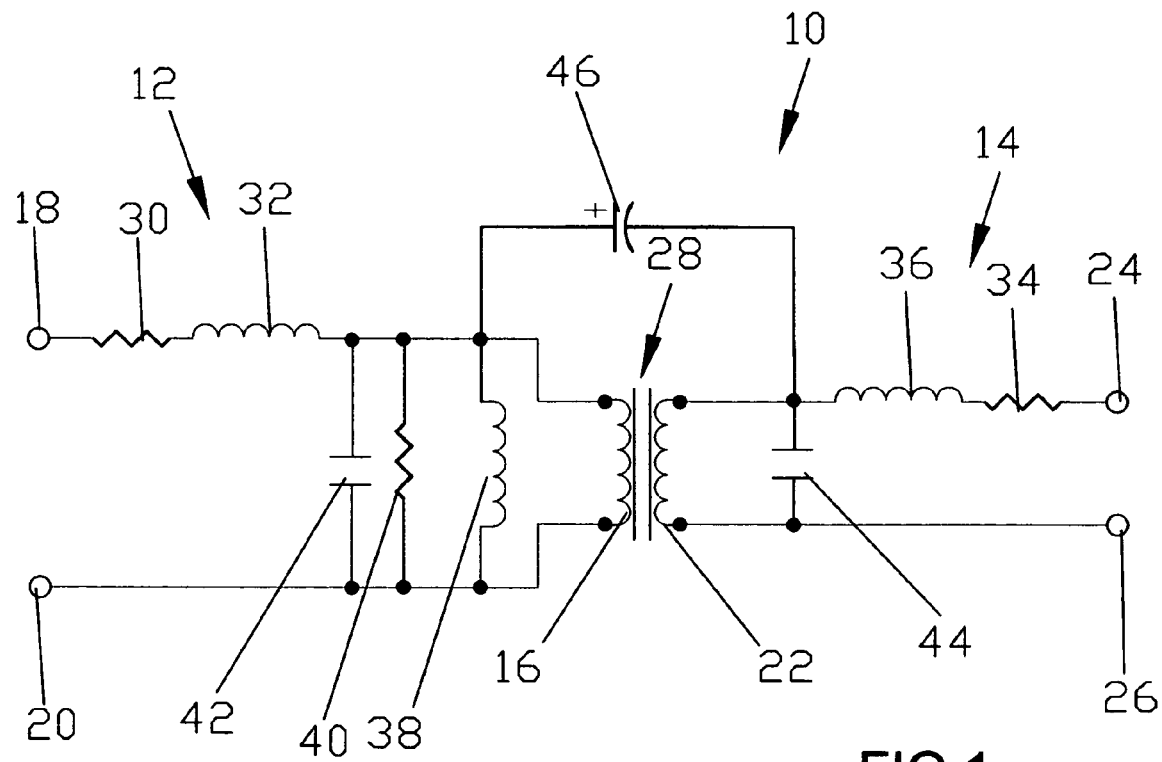
FIG. 1 is a schematic of an ideal transformer.

FIG. 1 depicts an equivalent schematic of a transformer generally indicated as 10 comprising an input section generally indicated as 12 and an output section generally indicated as 14.

The input section 12 comprises a primary winding 16 coupled across primary input and output terminals 18 and 20; while, the output section 14 comprises a secondary winding 22 coupled across secondary input and output terminals 24 and 26. A transformer core section generally indicated as 28 is disposed in operative relationship relative to the primary and secondary windings 16 and 22.

Primary stray resistance and primary stray inductance are represented as 30 and 32, respectively; while, secondary stray resistance and secondary stray inductance are represented as 34 and 36 respectively.

Primary excitation inductance, magnetic resistive core loss and primary winding capacitance are shown as 38, 40 and 42 respectively; while, secondary winding capacitance is shown as 44. Stray capacitance of the transformer 10 is depicted as 46.

In an ideal output transformer 12 for use in an electrosurgical device (not shown), the primary and secondary stray resistance 30 and 34, primary and secondary stray inductance 32 and 36, stray capacitance 46, primary and secondary winding capacitance 42 and 44, and magnetic resistive core loss 40 should be at or approach zero. Further, the primary excitation inductance 38 should be large enough for the operating frequency. A resonant output circuit may be preferable to provide a true sinusoidal waveform output over a range of operating loads such as from about 10 ohms to about 1000 ohms. The use of planar ferrite cores and windings generally provide excellent design parameters.

Figure 2:
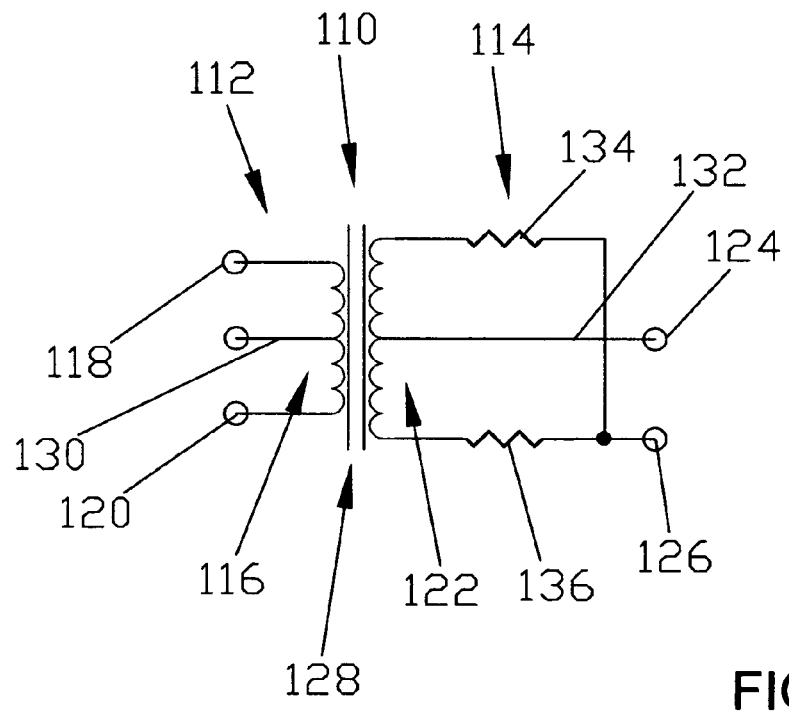
FIG. 2 is a schematic of a tapped transformer.

FIG. 2 shows a typical transformer having a single magnetic circuit generally indicated as 110 comprising an input section generally indicated as 112 and an output section generally indicated as 114.

The input section 112 comprises a primary winding 116 coupled across primary input and output terminals 118 and 120; while, the output section 114 comprises a secondary winding 122 coupled across secondary input and output terminals 124 and 126. A transformer core section generally indicated as 128 is disposed in operative relationship relative to the primary and secondary windings 116 and 122.

The primary winding 116 and the secondary winding 122 are tapped by conductors 130 and 132 respectively. Both ends of the secondary winding 122 are electrically coupled to the secondary output terminal 126; while, the mid-portion of the secondary winding 122 is electrically coupled to the secondary input terminal 124 by a conductor 132. The impedance representing the parasitic and external components are indicated as 134 and 136.

Instead of a single magnetic configuration as shown in FIG. 2, the transformer of the present invention is split to minimize the stray capacitance and reduce the negative effects of the other operating parameters commonly associated by transformers. In particular, the present invention relates to a planar push-pull output transformer and circuit as shown in FIGS. 3 and 4.

Figure 3:
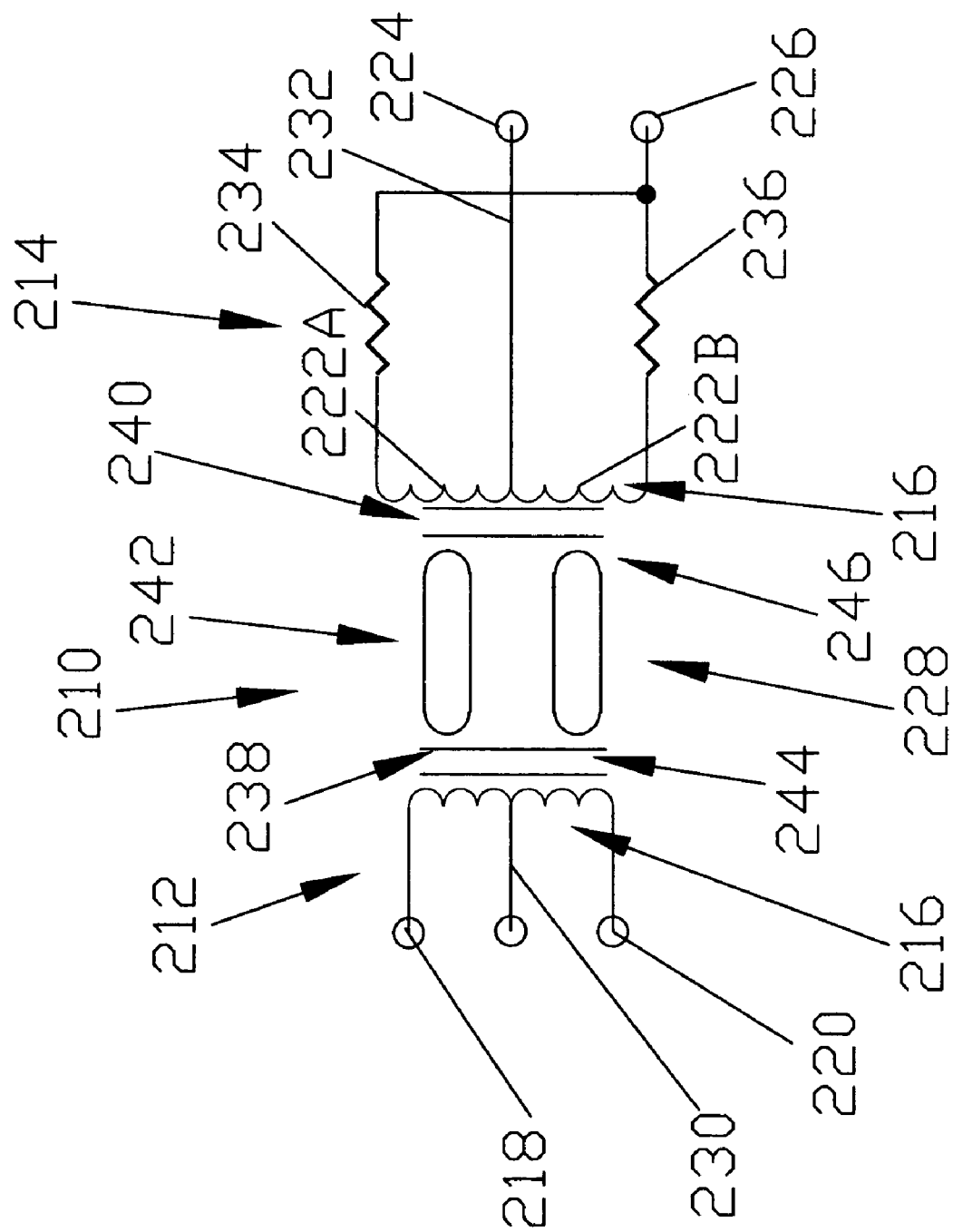
FIG. 3 is a schematic of a tapped step-down, step-up transformer.
Figure 4:
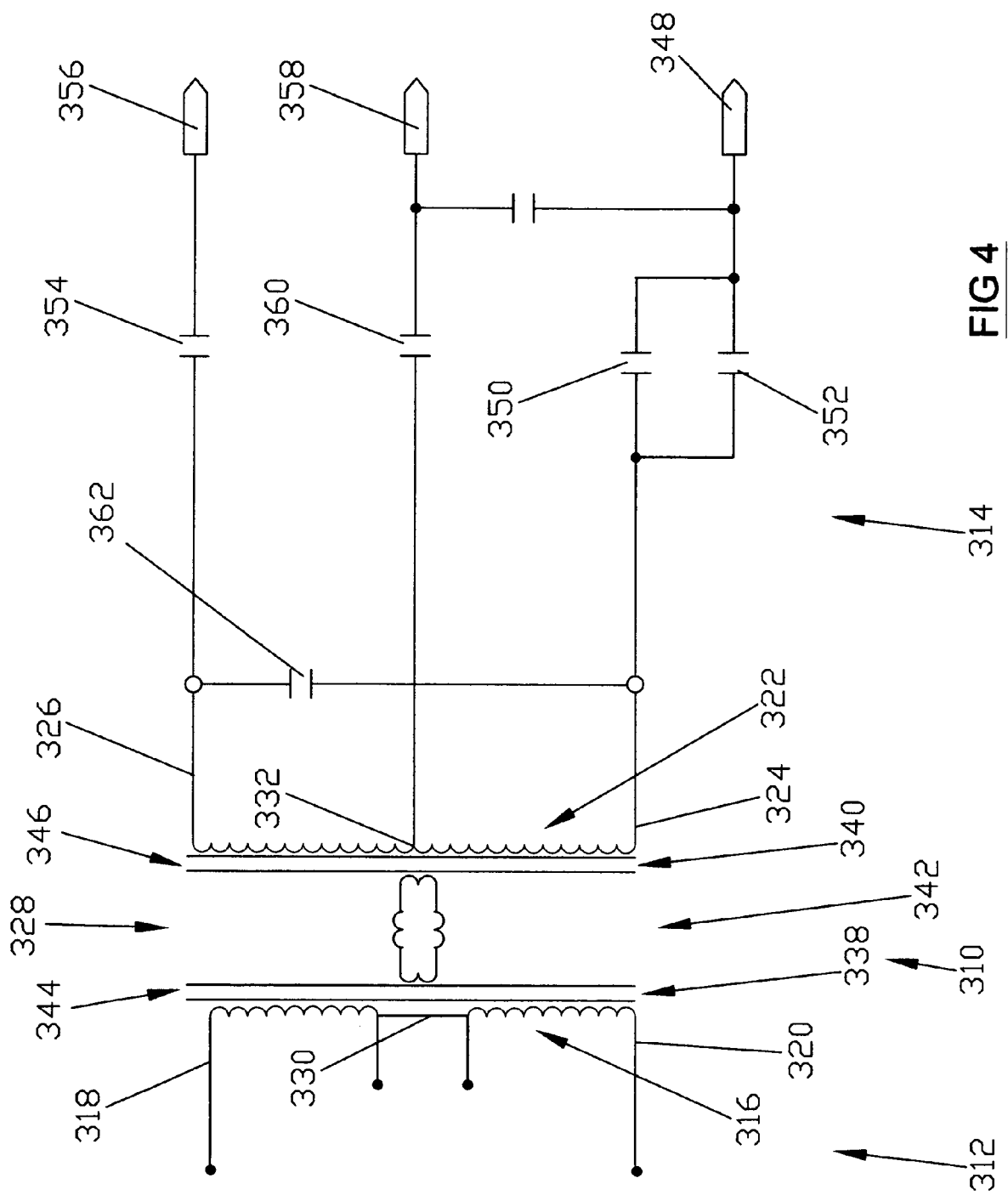
FIG. 4 is a circuit diagram of a step-down, step-up transformer of the present invention.

Specifically as shown in FIG. 3, the planar push-pull transformer generally indicated as 210 comprises an input section generally indicated as 212 and an output section generally indicated as 214.

The input section 212 comprises a primary winding 216 coupled across primary input and output terminals 218 and 220; while, the output section 214 comprises a secondary winding 222 coupled across secondary input and output terminals 224 and 226. A transformer core section generally indicated as 228 is disposed in operative relationship relative to the primary and secondary windings 216 and 222.

The primary winding 216 and the secondary winding 222 are tapped by conductors 230 and 232 respectively. Both ends of the secondary winding 222 are coupled electrically to the secondary output terminal 226; while, the mid-portion of the secondary winding 222 is electrically coupled to the secondary input terminal 224 by a conductor 232. The impedance representing the parasitic and external components including stray inductance and winding capacitance are indicated as 234 and 236.

The transformer core section 228 comprises a first core 238 and a second core 240 disposed in operative relationship relative to the primary winding 216 and the secondary winding 222 respectively and inductively coupled to each other by windings 242 to cooperatively form a step-down transformer segment 244 and a step-up transformer segment 246.

There are a number of operating advantages inherent in the step-down/step-up transformer configuration shown in FIG. 3 including minimizing the stray capacitance to about 5 pF represented as 46 in FIG. 1. In addition, the use of a planar implementation further reduces the stray capacitance since the distance between adjacent layers is relatively small, e.g. (value/measure). Furthermore, increased inductance leakage couples the transformer in a bridge filter. This filtering of the output waveform creates a more sinusoidal waveform reducing the leakage currents. Also, the two secondary winding segments 222A and 222B of the secondary winding 222 can be wound simultaneously or immediately adjacent each other increasing the secondary winding capacitance. Since the secondary winding 222 is bifilar, the two secondary winding segments 222A and 222B are substantially identified enhancing the effective filtering of the transformer bridge filter. In addition, means could be provided to increase the inductance of lines 242, 228 (FIG. 3). This inductance is effectively transformed by the step-up transformer 240, adding additional inductance value to the impedances 234 and 236. Thus, a substantially sinusoidal waveform is achieved for a very wide range of load impedances from about 5 ohms to an open circuit. The line inductance of 242 and 228 can be implemented by placing the conductors in ferrite planar cores or ferrite tubes.

In addition, this configuration increases the isolation breakdown voltage that can be as high as 10 kv. Finally, the planar ferrite core allows the use of cooling heat sinks disposed in heat exchange relationship to the flat surface of the planar core. This aspect can be significant when the transformer 210 is operating at high currents.

FIG. 4 shows the details of a planar, bifilar push-pull/step-down, step-up resonant transformer generally indicated as 310 comprising an input section generally indicated as 312 and an output section generally indicated as 314.

The input section 312 comprises a primary step-down winding generally indicated as 316 coupled to primary input and output terminals 318 and 320; while, the output section 314 comprises a secondary step-up winding generally indicated as 322 coupled across secondary input and output terminals 324 and 326. A transformer core section generally indicated as 328 is disposed in operative relationship relative to the primary and secondary windings 316 and 322. The primary winding 316 and the secondary winding 322 are tapped at 330 and 332 respectively.

The transformer core section 328 comprises a first core 338 and a second core 340 disposed in operative relationship relative to the primary winding 316 and the secondary winding 322 respectively and inductively coupled to each other by windings 342 to cooperatively form a step-down transformer segment 344 and a step-up transformer segment 346.

The present invention is implemented to reduce or minimize the stray capacitance as detailed in the circuit shown in FIG. 4. On the output side of the transformer core section 328, the secondary input terminal 324 is coupled to a return electrode 348 through capacitors 350 and 352. The secondary output terminal 326 is coupled through capacitors 354 to a first or primary active electrode 356; while, the tap 332 is coupled to a second or secondary active electrode 358 through capacitor 360. In addition, the secondary output terminal 326 is coupled to the secondary input terminal 324 through a capacitor 362.

In summary, the planar transformer power supply of the present invention as shown in FIG. 4, minimizes the capacitance to about 5 pF and increases the leakage inductance acting as a bridge filter. This provides additional filtering of the output waveform to move closely represent a sinusoidal waveform thus reducing the leakage currents. Also the configuration improves the isolation breakdown voltage of the transformer, are requirement which could be up to 10 kV.

In addition, the use of planar ferrite cores allows cooling heat-sinks to be attached easily to the flat surface of the planar core.

Finally, utilizing the planar transformer provides a resonance mode output stage.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A planar transformer power supply for an electrosurgical device to minimize stray capacitance comprising an isolation transformer and circuitry to limit the effects of a short circuit in the output of said planar transformer power supply to enhance power capacity at a low load impedance including a planar, bifilar push-pull/step-down, step-up resonant transformer comprising an input section and an output section, said input section comprises a primary step-down winding coupled to primary input and output terminals and said output section comprises a secondary step-up winding coupled across secondary input and output terminals, a transformer core section is disposed in operative relationship relative to said primary step-down winding and said secondary step-up winding, said primary step-down winding and the secondary step-up winding are tapped, said transformer core section comprises a first core and a second core disposed in operative relationship relative to said primary step-down winding and said secondary step-up winding and inductively coupled to each other by windings to cooperatively form a step-down transformer segment and a step-up transformer segment on the output side of said transformer core section, said secondary input terminal is coupled to a return electrode through a pair of parallel capacitors, said secondary output terminal is coupled through capacitors to a first or primary active electrode, said secondary tap is coupled to a second or secondary active electrode through a capacitor and said secondary output terminal is coupled to said secondary input terminal through a capacitor to reduce stray capacitance.

* * * * *